Figure 1:
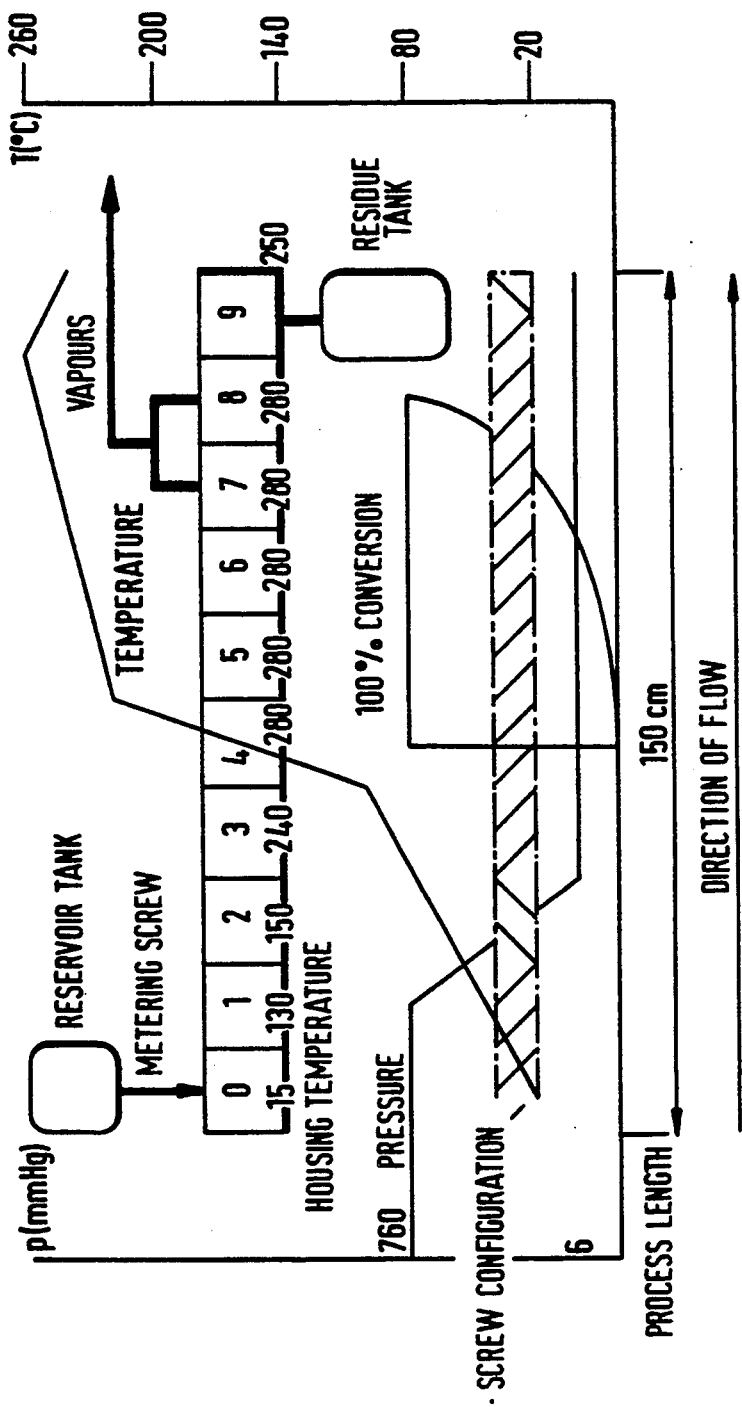
Figure 2:
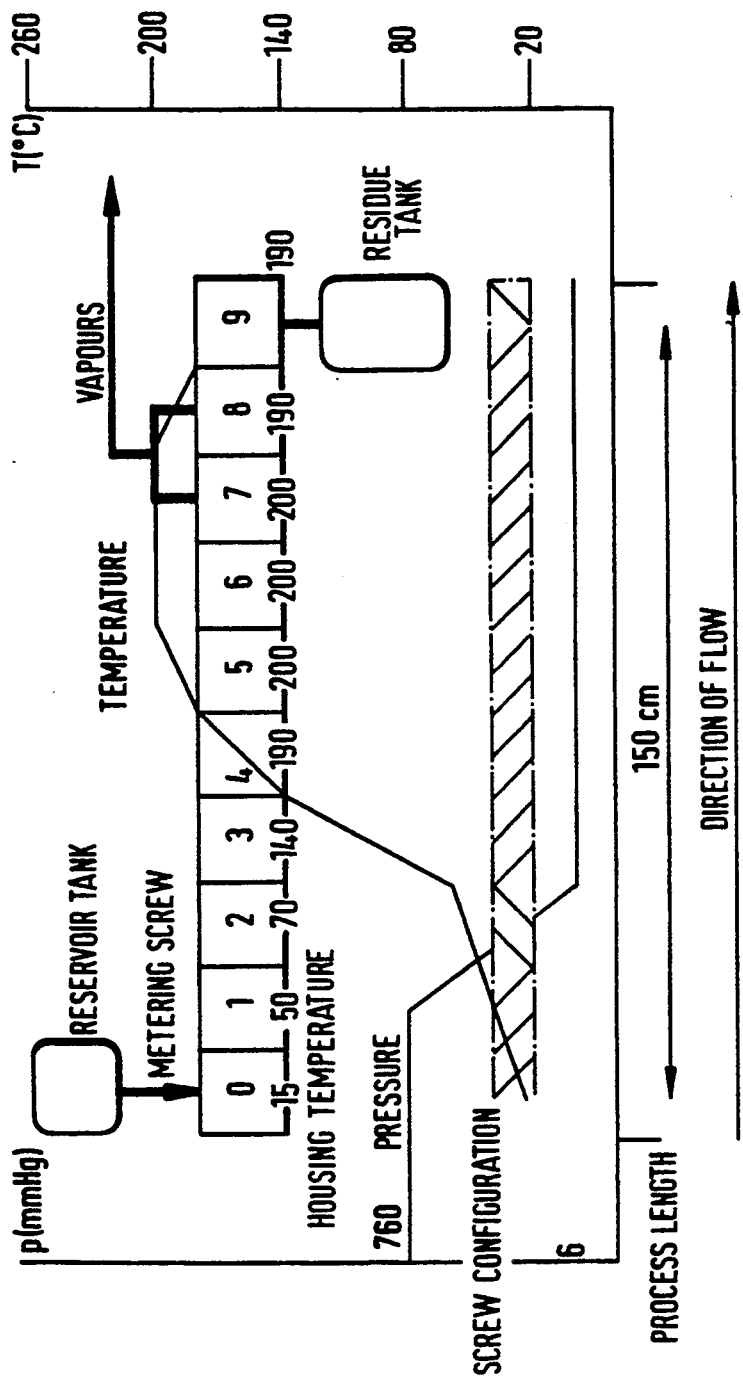

United States Patent [19]
Aigner et al.

[11] Patent Number: 5,347,020
[45] Date of Patent: Sep. 13, 1994

[54] PROCESS FOR THE PREPARATION AND PURIFICATION OF THERMOLABILE COMPOUNDS

[75] Inventors: Michael Aigner; Wolfgang Dersch; Dieter Reichert, all of Ingelheim am Rhein; Horst Schwall, Gau-Algesheim; Werner Warth, Ingelheim am Rhein, all of Fed. Rep. of Germany

[73] Assignee: Boehringer Ingelheim GmbH, Ingelheim am Rhein, Fed. Rep. of Germany

[21] Appl. No.: 13,517

[22] Filed: Feb. 3, 1993

Related U.S. Application Data

[60] Continuation of Ser. No. 868,921, Apr. 15, 1992, abandoned, which is a continuation of Ser. No. 613,185, Nov. 13, 1990, abandoned, which is a division of Ser. No. 112,849, Oct. 23, 1987, Pat. No. 4,990,222.

[30] Foreign Application Priority Data

Oct. 24, 1986 [DE] Fed. Rep. of Germany ....... 3636188
Oct. 24, 1986 [DE] Fed. Rep. of Germany ..... 36361987
Jul. 28, 1987 [DE] Fed. Rep. of Germany ....... 3724933
Aug. 8, 1987 [DE] Fed. Rep. of Germany ....... 3726499

[51] Int. Cl.$^5$ ............................................ C07D 319/00
[52] U.S. Cl. .................................................... 549/274
[58] Field of Search ......................................... 549/274

[56] References Cited

U.S. PATENT DOCUMENTS

| | | | |
|---|---|---|---|
| 4,835,293 | 5/1989 | Bhatia | 549/274 |
| 4,990,222 | 2/1991 | Aigner et al. | 549/274 |
| 5,043,458 | 8/1991 | Bhatia | 549/274 |

*Primary Examiner*—C. Warren Ivy
*Assistant Examiner*—A. A. Owens
*Attorney, Agent, or Firm*—David E. Frankhouser; Alan R. Stempel; Mary-Ellen M. Timbers

[57] ABSTRACT

The invention relates to a new process for the preparation and purification of thermolabile compounds.

4 Claims, 2 Drawing Sheets

PROCESS FOR THE PREPARATION AND PURIFICATION OF THERMOLABILE COMPOUNDS

This is a continuation of application Ser. No. 868,921, filed Apr. 15, 1992, which is a continuation of application Ser. No. 613,185, filed Nov. 13, 1990, now abandoned, which is a division of application Ser. No. 112,849, filed Oct. 23, 1987, now U.S. Pat. No. 4,990,222.

The invention relates to a process for the preparation and purification of thermolabile viscous compounds, in particular glycolides.

In the context of the invention, glycolides are the cyclic six-membered diesters of α-hydroxycarboxylic acids of the general formula

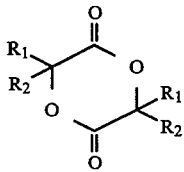

wherein $R_1$ and $R_2$, which can be identical or different, can denote hydrogen or a branched or unbranched alkyl radical with up to 16 carbon atoms, such as e.g. methyl, ethyl, n-propyl, iso-propyl, n-butyl, iso-butyl, tert.butyl and others.

Glycolides, in particular glycolide (1,4-dioxane-2,5-dione) itself, and lactides are used, inter alia, as starting substances for the preparation of biologically degradable medical auxiliary materials based on polyesters. Both polyglycolide (1,4-dioxane-2,5-dione) and polylactide themselves and the copolymers of lactides with other glycolides, in particular 1,4dioxane-2, 5-dione and other reaction partners capable of polymerization, are used.

The preparation of glycolides is described in the literature.

Examples of known preparation processes for glycolide (1,4-dioxane-2,5-dione) are those based on glycolic acid (DE-A-16 68 993 and DE-A-16 68 994), halogenoacetic acids (F. Andreas et al., J. Pr. Chem. 18, 141 (1962)) and salts thereof, polyglycolic acid, glycolic acid esters (FR 14 85 302), chloroacetyl-glycolic acid salts (U.S. Pat. No. 3,763,190) and chloroacetylpolyglycolic acid (J. Am. Chem. Soc. 76, 754 (1954)), or, generally, preparation processes based on α-halogenocarboxylic acids, α-hydroxycarboxylic acids and derivatives thereof, such as e.g. α-hydroxycarboxylic acid esters, and poly-α-hydroxycarboxylic acids. In the case of the monomeric educts, a polyester is first formed, and is then subjected, in situ or after isolation, to further reaction to give the dimer. This reaction consists of thermolysis at 200°-300° C. with the addition of metals, metal oxides or salts. The dimers thereby formed are distilled off—preferably under a vacuum. The distillate is converted into a stable form in purification steps which are to be carried out several times, such as e.g. crystallization from suitable solvents. Such a procedure is described for lactide, for example, in British Patent 1 007 347.

The thermolysis disclosed in that patent is, because of the properties of the starting material and reaction product, a hazardous reaction which is to be classified as a reaction with a high safety risk due to the possible danger of explosion. The thermodynamic study of the reaction shows that the reaction temperature required for formation of glycolide from polyglycolic acid or of lactides from polylactic acids lies in the region of thermal decomposition of the compounds to give gaseous secondary products. The exothermicity of the decomposition reaction is compensated by the vaporization enthalpy of the glycolides formed. It follows that the reaction can then lead to thermo-explosion of the reaction mixture if the vaporization of the glycolides for whatever reason—is no longer guaranteed, such as e.g. in the event of a breakdown in the vacuum, blockage of the lines etc. The course of the conventional thermolysis process under batch conditions is outlined below using the example of glycolide or lactide.

The low molecular weight polylactic acid (polyglycolic acid) used as the starting substance is mixed with the catalyst and the mixture is introduced into the reaction apparatus and heated up to the required reaction temperature of 240°-260° C. During the heating up operation, the starting substance melts, and at 240° C. the lactide (glycolide) starts to distil off. After a short time the reaction mixture becomes dark in colour and is transformed into a viscous state. From this point in time, the reaction mixture is no longer perfectly homogenised. The inhomogeneous reaction mixture tends towards uncontrolled decomposition, since local foci of overheating may develop. The reaction residue which remains in the reaction mixture when the reaction has ended must be removed from the reaction vessel by prolonged heating in concentrated sodium hydroxide solution.

Because of the inhomogeneous reaction conditions, varying qualities and yields are achieved in batchwise thermolysis. The yield of distillate, i.e. of crude lactide, is 70-90% of theory t.q. After working up of the distillate by precipitation in a suitable organic solvent, such as e.g. alcohols ($C_1$ to $C_4$) or halogenated hydrocarbons (e.g. carbon tetrachloride), a yield of 40-60% of theory is obtained. DE-A-15 43 958 quotes a yield of, for example, 56% in the thermolysis, but the subsequent purification steps have not yet been taken into consideration.

Surprisingly, the disadvantages described above for the preparation process known from the literature can be avoided with the process according to the invention.

The process is characterized in that the reaction is carried out continuously under forced conveyance into a reactor with a rising temperature gradient.

The product formed in the thermolysis is collected as the distillate and optionally subjected to further purification steps. Unreacted starting material and higher-boiling by-products are discharged from the reactor as a result of the forced conveyance.

The reaction can conveniently be carried out under an inert gas atmosphere and/or reduced pressure.

A suitable reactor such as can be used according to the invention is, for example, a self-cleaning twin-screw extruder with attached exhaust vapour lines.

Such apparatuses are known and find many applications in plastics production. The apparatuses are as a rule constructed by the modular principle and are marketed by a number of machine construction companies in comparable forms. Whereas in the plastics processing industry twin-screw extruders are used for homogenizing plastics granules, if appropriate with admixing of auxiliaries, such as fillers or pigments, and for generating the necessary admission pressure at the shaping die, in the case of the preparation of glycolides the extruder is used as a continuously operating chemical reactor.

The following advantages over known preparation processes result according to the invention.

As a result of the low thermolysis volume, the reaction mass is kept small. Trouble or hazards due to pressure build-up during the reaction are therefore insignificant and require no special measures. The twin screw of the extruder ensures on the one hand perfect homogenisation of the reaction mixture and thus a uniform reaction temperature over the cross-section of the flow tube, and on the other hand forced discharge of the polymeric material always formed by side reactions, and furthermore a suitable arrangement of the twin screw ensures continuous self-cleaning of the reactor, which means that sticking of the reaction mixture to components of the reactor is avoided, since the residue is transported forcefully by the twin screw into the residue tank. A continuous thermolysis procedure is thereby rendered possible. The twin screw of the extruder furthermore ensures perfect homogenization of the reaction mixture and thus a constant, controlled temperature programme.

The construction of such an extruder is shown schematically in FIG. I.

This figure illustrates the principle of the reaction procedure in the flow tube with forced conveyance in a twin-screw extruder.

The extruder has devices which allow separate heating of the individual segments, so that a temperature gradient can be built up, heating being carried out, for example, according to the following plan:

| Housing no. | Temp °C. |
| --- | --- |
| 0 | 15 |
| 1 | 130 |
| 2 | 150 |
| 3 | 240 |
| 4 | 280 |
| 5 | 280 |
| 6 | 280 |
| 7 | 280 |
| 8 | 280 |
| 9 | 250 |

The number of heating segments can of course be varied if a more differentiated temperature programme is required.

The exhaust vapour lines with which the product is collected as distillate are located above housings no. 7 and 8. The apparatus furthermore consists of a reservoir tank and a residue tank, and of devices for maintaining a vacuum. The starting material is conveyed via a metering screw into the actual reactor, in which a twin screw on the one hand effects forced conveyance through the reactor and on the other hand ensures homogeneous mixing of the plastic reaction mixture and also self-cleaning during the entire course of the reaction.

Description of the process:

The poly-hydroxycarboxylic acids used in the depolymerization reaction are prepared as described in the literature, see e.g. Chem. Ber. 58, 1307 (1925).

For example, commercially available optically active [R], [S] or racemic lactic acids are dehydrated by distillation under a vacuum up to a sump temperature of 200° C. Oligomeric lactic acids are thereby formed. These lactic acids are liquid at elevated temperature and solidify on cooling to room temperature to give vitreous masses which can be comminuted by the customary mechanical methods. The powders or granules obtained in this way are mixed with a suitable catalyst and the mixture is introduced into the product feed of the extruder using a solids dosage device.

The twin screw conveys the reaction mass through the flow tube. Behind the screw, by suitable choice of the speed, feed and temperature, a consistency of the reaction mass is established such that a vacuum of 2–5 mbar on the distillation side is maintained. The backpressure in the flow tube can be brought about by suitable choice of the screw configuration, e.g. by changing the screw pitch, or by reversing the conveying direction. (FIG. I shows the screw configuration of a screw schematically; the expert is sufficiently familiar with the technical realization of a corresponding self-cleaning twin screw.) The reaction mass then passes through a temperature gradient of 130°–280° C. Thermolysis of the low molecular weight polyglycolide to give glycolide thereby takes place. Evaporation takes place under the exhaust vapour openings, the resulting distillate is removed to a heated reservoir tank and the residue which remains makes up about 5 wt. % of the amount introduced and is conveyed forcedly by the screw into the residue discharge tank, so that continuous operation is rendered possible. In carrying out the process, it proves to be advantageous if the heating segment after the exhaust vapour lines (heating segment 9 in FIG. I) has a lower temperature than that on the exhaust vapour lines; this ensures that the polymeric material formed by side reactions is solidified and discharged. If desired further exhaust vapour lines can be attached in regions of lower temperatures in order to remove low-boiling impurities.

The process described above can be carried out on an industrial scale. The yield of distillate (crude glycolide) is about 95.0% of theory t.q.

Description of the apparatus

The extruder is equipped with a metering screw for feeding-in solid on the feed side, and furthermore with a heated exhaust vapour tube, a condenser, two interchangeable vacuum receivers for vacuum distillation and a vacuum-proof discharge tank which collects the reaction residue. Details of the apparatus can be seen from the flow chart included for the process (FIG. I). The apparatus also has devices for generating and maintaining the necessary vacuum of 2 to 5 mbar. The segments 0 to 9 designate parts of the reactor which can be heated independently of one another, which means that the necessary temperature gradient can be produced.

The screw is designed so that, as a result of the plastic material, a vacuum can be maintained without problems in a certain section of the reactor. FIG. I illustrates the pressure pattern within the reactor.

Glycolides of the general formula I wherein $R_1$ and $R_2$ have the meanings given below are preferably prepared in the process according to the invention.

| $R_1$ | H | H | $CH_3$ | $C_2H_5$ | $CH(CH_3)_2$ |
| --- | --- | --- | --- | --- | --- |
| $R_2$ | H | $CH_3$ | $CH_3$ | H | H |
| $R_1$ | $C_2H_5$ | $n-C_4H_9$ | $C(CH_3)_3$ | $nC_5H_{11}$ | $nC_7H_{15}$ |
| $R_2$ | $CH_3$ | H | H | H | H |

-continued

| R₁ | n—C₁₂H₂₅ | n—C₁₅H₃₁ | n—C₁₃H₂₇ | n—C₁₄H₂₉ |
|---|---|---|---|---|
| R₂ | H | H | H | H |
| R₁ | n—C₁₆H₃₃ | | | |
| R₂ | H | | | |

To prepare glycolide (1,4-dioxane-2,5-dione) in the process according to the invention, a low molecular weight (oligomeric) polyglycolide or a halogenoacetic acid salt, for example, is used as the starting material and is introduced into the reservoir tank (see FIG. I) together with a suitable catalyst. The preparation of low molecular weight polyglycolide is generally known, and is thus carried out e.g. by heating halogenoacetic acids and/or sodium chloroacetate in xylene. Suitable catalysts for the depolymerization are likewise prior art, for example tin and zinc or their compounds. A preferred catalyst is zinc oxide. Between 0.01 and 4 wt. % catalyst is in general used. The educts are then introduced into the extruder by means of a metering screw and are reacted as described above.

The thermolysis in the process described above can be transferred to the industrial scale. The yield of distillate (crude glycolide) is 95% of theory t.q. After working up by precipitation in isopropanol, a yield of 81% of theory results. The increase in yield over the batch process is on average about 60%. The product is passed to a further purification process which leads to a glycolide quality which is suitable for the preparation of high molecular weight polyesters such as are used e.g. for the production of surgical suture material.

The new process carried out in a self-cleaning flow tube with forced conveyance (twin-screw extruder) is distinguished in particular by the following advantages over the processes described in the literature:
  problem-free practicability of the reaction due to the forced discharge of polymeric material formed,
  higher-yield,
  better product quality,
  high safety in carrying out this reaction with a high hazard class because of the very small thermolysis volume in the flow tube and the resulting very small reaction mass,
  very low-polluting.

As a result of the high yield and the special process technology, only minimal amounts of solid waste products are obtained. The large amounts of strongly alkaline effluents formed in the batch process are avoided.

The new continuously operating process now renders it possible to prepare glycolides in a conventionally equipped chemical factory without particularly expensive safety installations.

The above-mentioned preparation process is also suitable for the distillation of chemical compounds.

Distillation is a widely used method of purifying or separating organic and inorganic chemical substances (see R. Billet, "Industrielle Destillation" [Industrial Distillation], Verlag Chemie, Weinheim, 1973).

Distillations are frequently carried out under a vacuum, in order to reduce the exposure of the substances to heat by reducing the boiling point. Various technical embodiments belong to the prior art, including apparatuses for carrying out vacuum distillation by a continuous process. Apparatuses which permit the gentlest possible vacuum distillation of chemical substances are e.g. thin film evaporators and falling film evaporators of various construction and design. These distillation processes are used both for substance distillation in the actual sense and for removing more highly volatile secondary constituents, such as solvents or, in the case of polymeric substances, residual monomer. The desired product is found in the distillation residue in these cases. In cases where highly volatile constituents are to be removed from highly viscous mixtures by distillation, screw evaporators are also used in exceptional cases in industry (see Ullmann, "Enzyclopadie der technischen Chemie" (Encylopaedia of Industrial Chemistry), Volume 2, page 658 et seq.). Volatilization of monomers from polymeric material with the aid of screw evaporators is described, for example, by K.-M. Hess in Chem. Ing. Techn. 51 (3), 245 (1979).

The distillation of chemical substances in general finds its limits where the substances can no longer be evaporated without decomposition and high-boiling and highly viscous or solid, often polymeric by-products are formed by the decomposition content. In industrial distillation processes, these by-products lead to a number of problems, the cause of which lies in the formation of deposits (fouling) on the surfaces of the distillation apparatuses and heat exchangers. Heat transfer is impaired by deposit formation at the edges, and uniform evaporation of the substance no longer takes place. This fouling process is of great disadvantage particularly in all types of continuous evaporators, but especially in the continuous falling or climbing film evaporators of various design.

Surprisingly, it has been possible to eliminate the abovementioned known disadvantages in the distillation of thermolabile compounds using conventional processes by a procedure in which the substance to be distilled is distilled in a reactor (flow tube) with a rising temperature gradient under forced conveyance.

The process according to the invention is distinguished by the fact that chemical compounds which tend to decompose during distillation can be distilled, even at higher temperatures, optionally under a vacuum, with excellent yields and a reduced safety risk.

A number of substances, in particular organic compounds, which can be distilled in evaporators of the conventional type only with a poor yield and/or only under a high safety risk, if at all, can thus be distilled at a high temperature under a high vacuum within the thermal decomposition range of the substances.

The process according to the invention is described in more detail below. In the process according to the invention, the substance is distilled in a continuous process in a flow tube with forced conveyance, optionally under reduced pressure, optionally under an inert gas atmosphere, and under a rising temperature gradient. The substance is thereby conveyed with a very short residence time along a temperature gradient, whereupon it evaporates. The distillate is then precipitated with the aid of a suitable condenser system and isolated.

In a preferred embodiment, the flow tube consists of a twin-screw extruder, the twin screw taking over the functions of sealing off the vacuum from the atmosphere, forced conveyance and self-cleaning. The fouling deposit is removed from the heat-transferring walls by the twin screw and conveyed to the residue discharge tank.

The construction of an extruder which can be used for the distillation has already been shown essentially in FIG. I, but there are differences in the heating of the individual segments.

FIG. II shows schematically the construction of an extruder which is suitable for distillations.

The extruder has devices which allow separate heating of individual segments, so that a temperature gradient can be built up, heating being carried out, for example, in accordance with the following plan:

| Housing no. | Temp. °C. |
| --- | --- |
| 0 | 15 |
| 1 | 50 |
| 2 | 70 |
| 3 | 140 |
| 4 | 190 |
| 5 | 200 |
| 6 | 200 |
| 7 | 200 |
| 8 | 190 |
| 9 | 190 |

The exhaust vapour lines with which the distillate is collected are located above housings no. 7 and 8. The apparatus furthermore consists of a reservoir tank and a residue tank, and of devices for maintaining a vacuum. The substance to be distilled is fed from the reservoir tank into the flow tube, where it is heated to the boiling point as a result of forced conveyance, e.g. by a synchronously rotating twin screw, through segments of increasing temperature. The temperature programme depends on various factors, such as e.g the construction of the reactor (extruder), the speed, amount and nature of the material introduced, etc. In the region of the boiling point, the distillate is removed, whilst the higher-boiling residue is removed from the distillation region as a result of the forced conveyance. For carrying out the process, it is advantageous if the heating segments downstream of the exhaust vapour lines have a temperature below the boiling point of the distillate, so that the distillation residue solidifies when it is discharged as a result of the forced conveyance. Behind the screw, by suitable choice of the speed, feed and temperature, a consistency of the reaction mass can be established (see FIG. I) such that a reduced pressure can be maintained on the distillation side.

The backpressure in the flow tube can be brought about by suitable choice of the screw configuration, e.g. by changing the screw pitch, or by reversing the conveying direction. (FIG. I shows the screw configuration of a screw schematically; the expert is sufficiently familiar with the technical realization of a corresponding self-cleaning twin screw.) The resulting distillate is condensed and, optionally, further processed.

The number of heating segments, the temperature programme, the speed of the screw and the location and number of the exhaust vapour lines can of course be adapted to suit the specific distillation problem.

The process according to the invention is not limited exclusively to the distillation of liquid or viscous substances. Because of the forced conveyance of the substance, plastic or solid compounds can also be distilled or sublimed. It goes without saying here that the heating of the exhaust vapour line and also its construction is designed so that condensation of the product does not lead to blocking of the apparatus and, for example, first occurs in a suitable cold trap.

The temperature of the heating segments is determined by the heating medium used. Heating of the segments by oil follows. If the maximum heating segment temperature is about 300° C., about 400° C. can be achieved if electrical heating is used. Such heating systems are already commercially available. However, for specific problems, it is also conceivable to use specially manufactured products with segments which can be heated to higher temperatures. The distillation can be carried out under reduced pressure in order to reduce the boiling points. Depending on the construction, pressures down to a lower limit of about 0.5 mbar can be established.

The distillation process described above is suitable not only for the laboratory scale but also for distillations on an industrial scale.

The new process permits high temperature distillation of organic compounds of low volatility by a continuous procedure. The distillation process according to the invention is particularly suitable for the purification of compounds with which a higher-boiling component concentrates in the bottom product as an undesirable by-product in conventional distillation processes. The process is also suitable for distilling compounds off from solid residues.

The possibility is therefore provided of distilling, and hence purifying, without danger and in a high yield, substances which cannot be distilled under conventional conditions because of their thermolability.

In cases where recrystallization—sometimes several times—can be replaced by the new process, the environmental benefit of the distillation process is a further additional advantage:

Only very small amounts of residues, if any, are obtained, no emission arises and the effluent is not polluted.

The following examples are intended to illustrate the process according to the invention in more detail.

1. Apparatus
   Twin-screw metering unit for solids
   Twin-screw extruder with exhaust vapour removal and vacuum connection
   Glass condenser charged with heat transfer medium
   Vacuum receiver with double jacket
   Residue discharge tank with nitrogen compensation and vacuum connection
2. Process procedure
   The extruder is heated in accordance with the temperature gradients given in the examples.
   The exhaust vapour line is heated to the desired temperature and the double-jacketed glass receivers are heated with heat transfer medium to a temperature above the melting point of the appropriate compound.
   When the desired temperature is reached, the extruder is operated with the normal feed, as mentioned in the example, and the normal screw speed.
   The pressure during the distillation is 0.5 to 1,025 mbar, preferably 2–10 mbar. After flushing of the vacuum receivers with nitrogen, the distillate is drained off into a thermal vessel and passed to a suitable method of working up, such as e.g. granulation in a non-solvent or solidification by cooling by means of a belt or rollers.

The process according to the invention is particularly suitable for the purification of glycolide (1,4-dioxane- 2,5-dione), a glycolide of very high purity which can be used for polymerization without further purification measures being obtained.

The condensed distillate of pure glycolide obtained by the process according to the invention is then precipitated in a non-solvent, e.g. petroleum ether. The crystal suspension thus obtained is separated off and dried. It is also possible, and desirable on an industrial scale, to allow the distillate to solidify directly via a cooling device, such as e.g. a cooling roller or cooling belt. The indirect route via granulation in an inert solvent and the subsequent separation and drying step is thereby avoided.

If desired, or if it appears to be necessary, low-boiling impurities of the crude glycolide can be removed by additional exhaust vapour lines in the lower temperature regions.

The process according to the invention renders possible the continuous distillation of crude glycolide on an industrial scale, between 95 and 98 wt. % (based on the crude glycolide employed) highly pure glycolide such as it has not been possible to prepare in this purity on an industrial scale by processes known hitherto being obtained.

The purification processes known from the prior art, whether recrystallisation or sublimation, give a glycolide which differs in its substance properties from the glycolide prepared by the process according to the invention. Thus, for example, batchwise distillation processes cause a greater exposure of the glycolide to heat and lead to a higher content of decomposition products, which are also deposited on the cooling surface during sublimation and can no longer be removed from the glycolide.

Whereas a glycolide (1,4-dioxane-2,5-dione) prepared by known purification processes can be polymerised to give a polyglycolide with an intrinsic viscosity of about 1 [dl/g], a polyglycolide with an intrinsic viscosity of $>1.4$ [dl/g] is obtained under identical polymerization conditions (e.g. $SnCl_2 \times H_2O$, lauryl alcohol) from a glycolide prepared by the process according to the invention. (The intrinsic viscosities are determined in hexafluoroisopropanol at 30° C.).

EXAMPLE 1

Continuous preparation of glycolide from low molecular weight polyglycolide with catalytic amounts of zinc oxide 2 wt. % zinc oxide is added to low molecular weight polyglycolide and the mixture is homogenised in a suitable mixing apparatus, such as e.g. a gyrowheel mixer.

| Housing no. | 0 | 1 | 2 | 3 | 4 | 5 | 6 | 7 | 8 | 9 |
|---|---|---|---|---|---|---|---|---|---|---|
| Temperature (°C.) | 15 | 130 | 150 | 240 | 280 | 280 | 280 | 280 | 280 | 250 |

The extruder is heated in accordance with the above table (see also FIG. I), the exhaust vapour line is heated at 180° C. and the vacuum receivers for collecting the distillate are heated at 80° C.

When the desired temperature is reached, the extruder is operated at a speed of 1.67/sec and a feed of 3.0 kg/hour low molecular weight polyglycolide under a pressure of 2–5 mbar. The vacuum receivers are emptied after periods of 60 minutes and the distillate is worked up. The yield of distillate is 95% of theory. The distillate is worked up conventionally by batchwise reprecipitation from isopropanol in a ratio of distillate/isopropanol = 1/2.5.

EXAMPLE 2

Continuous preparation of glycolide from sodium chloroacetate with catalytic amounts of zinc oxide 2 wt. % zinc oxide is added to sodium chloroacetate and the mixture is homogenised in a suitable mixing apparatus, such as e.g. a gyro-wheel mixer.

| Housing no. | 0 | 1 | 2 | 3 | 4 | 5 | 6 | 7 | 8 | 9 |
|---|---|---|---|---|---|---|---|---|---|---|
| Temperature (°C.) | 15 | 130 | 150 | 240 | 280 | 280 | 280 | 280 | 280 | 250 |

The extruder is heated in accordance with the above table (see also FIG. I), the exhaust vapour line is heated at 180° C. and the vacuum receivers for collecting the distillate are heated at 80° C.

When the desired temperature is reached, the extruder is operated at a speed of 1.33/sec and a feed of 3.3 kg/hour sodium chloroacetate under a pressure of 2–5 mbar. The vacuum receivers are emptied after periods of 60 minutes and the distillate is worked up as described in Example 1.

EXAMPLE 3

Continuous preparation of [S,S]-lactide from [S]-polylactic acid with catalytic amounts of zinc oxide 2 wt. % zinc oxide is added to [S]-polylactic acid and the mixture is homogenised in a suitable mixing apparatus, such as e.g. a gyro-wheel mixer.

The extruder is heated in segments at from 15° to 285° C. The exhaust vapour line is heated at 170° C. and the temperature of the vacuum receivers for collecting the distillate is 90° C. When the desired temperature is reached, the extruder is operated at a speed of 2.5/sec and a feed of 2.5 kg/hour [S]-polylactic acid under a pressure of 2–5 mbar. The vacuum receivers are emptied after periods of 60 minutes and the distillate is worked up.

The yield of distillate is 95% of theory. The distillate is worked up by batchwise reprecipitation from isopropanol in a ratio of distillate/isopropanol = 1/1.5.

EXAMPLE 4

Continuous preparation of [R,R]-lactide from [R]-polylactic acid with catalytic amounts of zinc oxide.

The preparation of the enantiomeric lactide follows the same procedure as described above for the optical antipode [S,S]-lactide.

EXAMPLE 5

Continuous preparation of [R,R],[S,S]-lactide (racemic lactide) and [R,S]-lactide (meso-lactide) from [R],[S]-polylactic acid with catalytic amounts of zinc oxide The preparation of the mixture of [R,R],[S,S]-lactide (racemic lactide) and [R,S]-lactide (meso-lactide) follows the same procedure as described for [S,S]-lactide.

The racemic lactide and meso-lactide are separated in a separate working up step.

EXAMPLE 6

Continuous distillation of [S,S]-3,6-dimethyl-1,4-dioxane-2,5-dione

| Housing no. | 0 | 1 | 2 | 3 | 4 | 5 | 6 | 7 | 8 | 9 |
|---|---|---|---|---|---|---|---|---|---|---|
| Temperature (°C.) | 15 | 50 | 70 | 140 | 190 | 200 | 200 | 200 | 190 | 190 |

The exhaust vapour line is heated at 140° C. and the double-jacketed glass receivers are heated at 95° C. with hot water.

When the desired temperature is reached, the extruder is operated with a feed of 5 kg per hour [S,S]-3,6-dimethyl-1,4-dioxane-2,5-dione at a screw speed of 1.67/sec. The pressure during the distillation is 2–4 mbar. After flushing with nitrogen, the distillate is drained into a thermal vessel and precipitated in petroleum ether 60/90 in a ratio of ¼ in a universal apparatus. The solid is removed via a centrifuge and dried in a vacuum drying cabinet.

The yield is 95–98% of the feed material.

EXAMPLE 7

Continuous distillation of [R,R]-3,6-dimethyl-1,4-dioxane-2,5-dione

The distillation of the [R,R]enantiomer of 3,6-dimethyl-1,4-dioxane-2,5-dione follows the instructions given in Example 3 for the [S,S] enantiomer of lactide.

EXAMPLE 8

Continuous distillation of [R,R],[S,S]-3,6-dimethyl-1,4-dioxane-2,5-dione

The distillation of the racemate of 3,6-dimethyl-i,4-dioxane-2,5-dione follows the instructions given in Example 3 for the [S,S] enantiomer.

EXAMPLE 9

Continuous distillation of [R,S]-3,6-dimethyl-1,4-dioxane-2,5-dione

The distillation of meso-3,6-dimethyl-1,4-dioxane-2,5-dione follows the instructions given in Example 3 for the [S,S] enantiomer of lactide.

EXAMPLE 10

Continuous distillation of 3-hydroxyacetophenone

| Housing no. | 0 | 1 | 2 | 3 | 4 | 5 | 6 | 7 | 8 | 9 |
|---|---|---|---|---|---|---|---|---|---|---|
| Temperature (°C.) | 15 | 25 | 55 | 105 | 180 | 180 | 180 | 180 | 180 | 250 |

The exhaust vapour line is heated at 170° C. and the double-jacketed glass receivers are heated at 90° C. with hot water.

When the desired temperature is reached, the extruder is operated with a feed of 4.3 kg per hour 3-hydroxy-acetophenone at a screw speed of 2.5/sec. The pressure during the distillation is 2–4 mbar. After flushing with nitrogen, the distillate is drained into a thermal vessel and precipitated in water in a ratio of ½ in a universal apparatus. The solid is separated off via a centrifuge and dried in a circulating air drying cabinet.

The yield is 91% of the feed.

EXAMPLE 11

Continuous distillation of 3-amino-2-chloropyridine

| Housing no. | 0 | 1 | 2 | 3 | 4 | 5 | 6 | 7 | 8 | 9 |
|---|---|---|---|---|---|---|---|---|---|---|
| Temperature (°C.) | 15 | 50 | 65 | 70 | 80 | 130 | 130 | 130 | 130 | 120 |

The exhaust vapour line is heated at 130° C. and the double-jacketed glass receivers are heated at 80° C. with hot water.

When the desired temperature is reached, the extruder is operated with a feed of 3.2 kg/hour 3-amino-2-chloropyridine at a screw speed of 0.83/sec. The pressure during the distillation is 2–4 mbar. After flushing with nitrogen, the distillate is drained into a thermal vessel and precipitated in water in a ratio of 1/1.4 in a universal apparatus. The solid is separated off via a centrifuge and dried in a circulating air drying cabinet. The yield is 85% of the feed.

EXAMPLE 12

Continuous distillation of glycolide (1,4-dioxane-2,5-dione)

| Housing no. | 0 | 1 | 2 | 3 | 4 | 5 | 6 | 7 | 8 | 9 |
|---|---|---|---|---|---|---|---|---|---|---|
| Temperature (°C.) | 15 | 50 | 70 | 140 | 190 | 200 | 200 | 200 | 190 | 190 |

The exhaust vapour line is heated at 140° C. and the double-jacketed glass receivers are heated at 85° C. with hot water. When the desired temperature is reached, the extruder is operated with a feed of 5 kg glycolide per hour at a screw speed of 1.67/sec. The pressure during the distillation is 2–4 mbar. After flushing with nitrogen, the distillate is drained into a thermal vessel and precipitated in petroleum ether 60/90 in a ratio of 1:4 in a 50 liter apparatus. The crystal suspension thus obtained is separated off via a centrifuge and dried in a vacuum drying cabinet. The yield is 95–98% of the feed. The material is suitable e.g. for the production of suture materials.

| Product description: | |
|---|---|
| Appearance: | white crystals |
| Smell: | almost odourless |
| Identity: | IR: α-form |
| Solubility: | readily soluble in acetone |
| | sparingly soluble in toluene |
| H₂O (Karl Fischer):0.01 | |
| Heavy metals: | >10 ppm |
| Free acid: | 0.02% |
| Content: | 99.8%–100.0% |
| Melting point: | 841° C. |
| (Differential thermal analysis) | |

What is claimed is:

1. A process for the preparation of a glycolide of the general formula

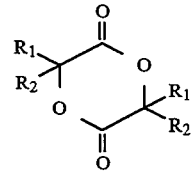

wherein $R_1$ and $R_2$ independently of one another are hydrogen or a branched or unbranched alkyl radical with up to 16 carbon atoms, from the corresponding low molecular weight poly-α-hydroxycarboxylic acid or an α-halogenocarboxylic acid salt in the presence of a catalyst, wherein the starting compound is subjected to thermolysis which is carried out continuously under forced conveyance in a reactor with a rising temperature gradient, and the glycolide formed is distilled off.

2. The process according to claim 1, wherein the temperature gradient rises from about 15° to 280° C. and thermolysis is carried out under a reduced pressure between about 0.1 to 5 mbar.

3. The process for the preparation of 1,4-dioxane-2,5-dione according to claim 2, wherein low molecular weight polyglycolides or halogenoacetic acid salts are used as the starting compound.

4. Poly-(1,4-dioxane-2,5-dione), having an intrinsic viscosity of 1.4 [dl/g], measured in hexafluoroisopropanol at 30° C.

* * * * *